United States Patent [19]

Styring, Jr.

[11] 4,246,015
[45] Jan. 20, 1981

[54] FREEZE-WASH METHOD FOR SEPARATING CARBON DIOXIDE AND ETHANE

[75] Inventor: Ralph E. Styring, Jr., Dallas, Tex.

[73] Assignee: Atlantic Richfield Company, Los Angeles, Calif.

[21] Appl. No.: 109,012

[22] Filed: Dec. 31, 1979

[51] Int. Cl.³ .............................................. F25J 3/02
[52] U.S. Cl. ....................................... 62/12; 62/532; 62/28
[58] Field of Search ............................. 62/12, 24–28, 62/532, 542

[56] References Cited

U.S. PATENT DOCUMENTS

| | | | |
|---|---|---|---|
| 3,130,026 | 4/1964 | Becker | 62/12 |
| 3,224,208 | 12/1965 | Schlumberger et al. | 62/12 |
| 3,236,057 | 2/1966 | Hashemi-Tafreshi | 62/12 |
| 3,376,709 | 4/1968 | Dickey et al. | 62/12 |
| 3,798,918 | 3/1974 | Maher et al. | 62/532 |

Primary Examiner—Norman Yudkoff
Attorney, Agent, or Firm—M. David Folzenlogen

[57] ABSTRACT

A method is disclosed for separating a mixture of carbon dioxide and ethane derived from a prior separation stage. The separation is accomplished by freezing the carbon dioxide in an azeotrope of carbon dioxide and ethane and washing the ethane from the solid carbon dioxide with a liquid hydrocarbon having at least three carbon atoms. The freezing stage may be preceded by distillation of a carbon dioxide-ethane mixture to form the azeotrope. The carbon dioxide and wash hydrocarbon may be separated in a subsequent distillation stage. In addition, if desired, the ethane-wash hydrocarbon mixture may be similarly separated in a subsequent distillation stage. The method is useful in carbon dioxide separation facilities where it is desirable to recover ethane that would otherwise be lost.

10 Claims, 1 Drawing Figure

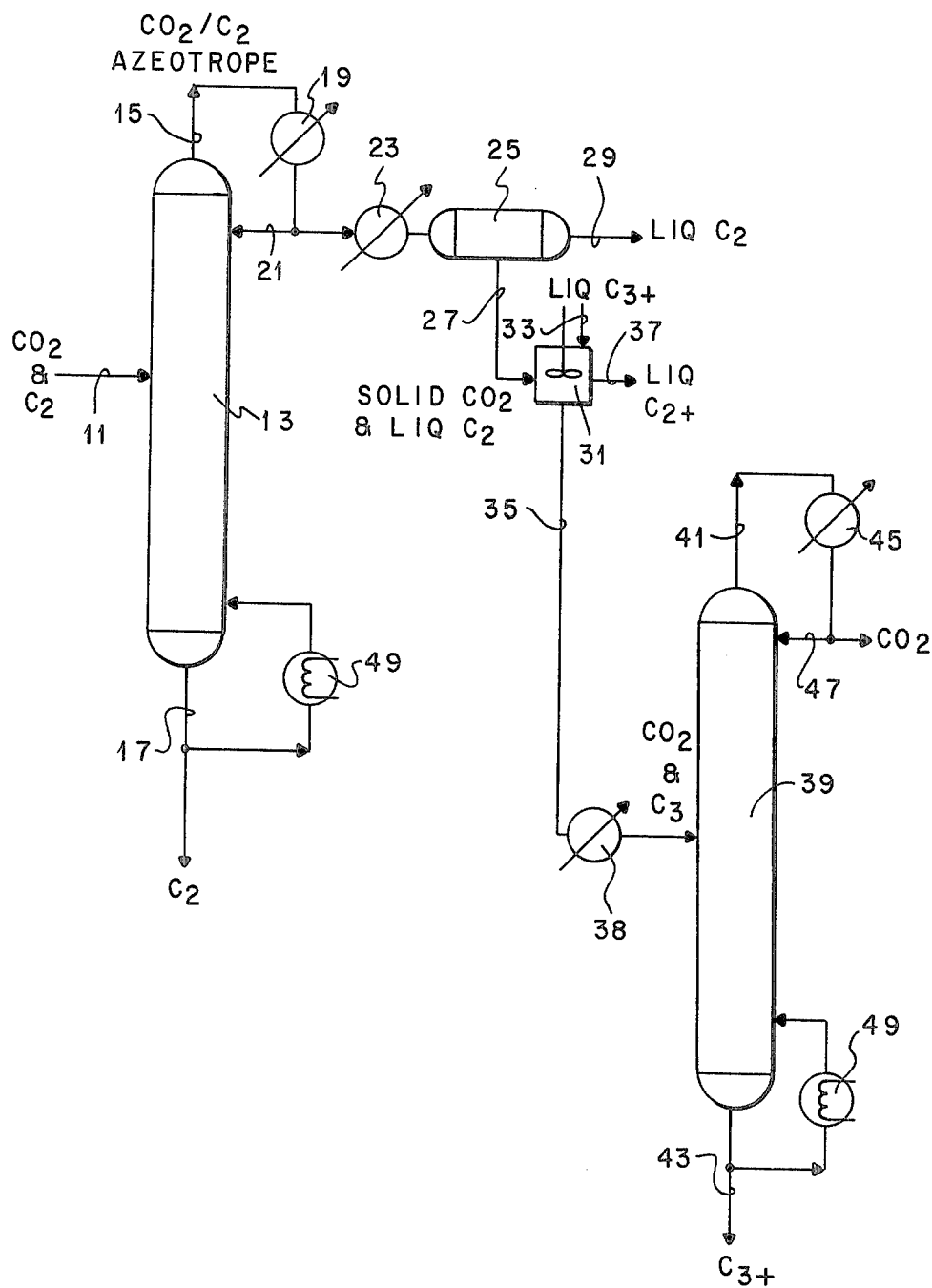

FREEZE-WASH METHOD FOR SEPARATING CARBON DIOXIDE AND ETHANE

BACKGROUND OF THE INVENTION

This invention is concerned with the separation of a mixture of carbon dioxide and ethane derived from a prior separation or recovery stage or process. More particularly, the invention pertains to separation of a carbon dioxide-ethane azeotrope by freezing the carbon dioxide and removing the ethane with propane or a heavier hydrocarbon.

It is sometimes desirable to separate carbon dioxide from a gaseous mixture containing ethane, for example, in the treatment of natural gas or a reservoir injection gas, or in the preparation of synthetic natural gas. In one or more stages of these processes, carbon dioxide, ethane and heavier hydrocarbons are separated or recovered as a mixture. It is then desirable to separate the carbon dioxide from the remaining hydrocarbons, sometimes called NGL (natural gas liquids). When carbon dioxide is distilled or fractionated from the hydrocarbons, an azeotrope of carbon dioxide and ethane is formed at an overhead point in the distillation column. At this point no more ethane is separated from the carbon dioxide. Generally, unless it is desirable to recover the carbon dioxide, the carbon dioxide is vented unless the concentration of ethane in the azeotrope is such that environmental regulations make it necessary to burn the ethane-carbon dioxide mixture. Flaring is frequently an expensive and difficult process, especially in areas where the amount and concentration of the gas being flared randomly varies with various operating or producing conditions. In processes where it is desirable to recover the carbon dioxide, for example, tertiary recovery processes, the unseparated ethane is lost.

The ethane in the carbon dioxide is a valuable hydrocarbon. This invention is concerned with separating and recovering ethane along with the other hydrocarbons that might be in a carbon dioxide-ethane mixture derived from a prior process.

SUMMARY OF THE INVENTION

A mixture of carbon dioxide and ethane derived from a prior separation stage or recovery process is separated by freezing the carbon dioxide in an azeotrope of ethane and carbon dioxide. Thereafter, the ethane is washed from the slurry with a wash liquid. The wash liquid is a liquid hydrocarbon with more carbon atoms than ethane, that is, a hydrocarbon having at least three carbon atoms. In the wash unit, ethane follows the heavier hydrocarbon.

The freezing stage may be preceded by a first stage distillation column operated to produce an azeotrope of carbon dioxide-ethane. The wash, ethane extraction stage may be followed by distillation of the mixture of carbon dioxide and wash hydrocarbon produced in the wash stage. In addition, if desired, the mixture of wash hydrocarbon and extracted ethane may also be separated in a subsequent distillation stage.

BRIEF DESCRIPTION OF THE DRAWING

The drawing is a schematic representation of a freeze-wash system for separating a mixture of carbon dioxide and ethane.

DETAILED DESCRIPTION

In the processing of gases containing carbon dioxide and ethane, for example, natural gas, there are times when it is necessary to remove carbon dioxide. For example, natural gas is predominantly methane. The methane is frequently mixed with carbon dioxide, ethane and other heavier hydrocarbons. After the methane is separated, the mixture of carbon dioxide, ethane and other hydrocarbons is processed to separate the carbon dioxide. It is well known that some of the ethane follows the carbon dioxide stream because ethane and carbon dioxide form an azeotrope. The composition of the ethane-carbon dioxide azeotrope depends on the operating conditions of the fractionation column. Conventionally, the distillation of a mixture of carbon dioxide and ethane will result in a carbon dioxide purity of only sixty-five to seventy-five mole percent. This ethane concentration is unacceptably high for venting the carbon dioxide. Moreover, if the volume of carbon dioxide is sufficiently large, the ethane is worth recovering. This disclosure pertains to separating carbon dioxide from ethane and any heavier hydrocarbons that might be present.

Accordingly, a mixture of carbon dioxide and ethane, with or without other hydrocarbons, is passed through feed inlet line 11 into first stage distillation column 13 at a point which is between overhead effluent line 15 and bottom liquid line 17. This mixture of carbon dioxide and ethane has been derived from a prior carbon dioxide separation stage or recovery process. For purposes of this disclosure, the previous stage or process is considered a carbon dioxide separation stage or recovery process if any fluid stream containing carbon dioxide and ethane is separated or developed. For example, the prior stage may have been a methane separation stage wherein a stream of carbon dioxide and ethane with or without heavier hydrocarbons is developed. The mixture may be gaseous, liquid, or a mixture of gas and liquid phases. Usually the mixture will be a two phase mixture at an elevated pressure. The pressure of the mixture will be at or above the pressure of the distillation column. The operation of distillation columns is well known and will not be discussed in detail.

During operation of column 13, an azeotrope of carbon dioxide and ethane will be formed in the upper rectification section of the column. This azeotrope exits the column through overhead effluent line 15. The concentration of carbon dioxide and ethane in the azeotrope will depend on the column overhead operating conditions. As shown, the carbon dioxide-ethane azeotrope overhead effluent fluids are cooled in first condenser 19 to condense all the overhead effluent fluids and form a liquefied azeotrope. Preferably, the condenser will be operated at a temperature above minus 69.9° F. to prevent the formation of solid carbon dioxide in this condenser. At least a part of the condensed overhead fluids is recycled to the column through reflux inlet line 21.

The ethane and heavier hydrocarbons in the feed mixture which are liquefied in the column are removed through bottoms liquid line 17 and recovered.

The azeotrope of carbon dioxide and ethane is passed through chiller 23 to freeze the carbon dioxide in the azeotrope. The chiller will be operated at a temperature below the triple point of carbon dioxide, that is, below minus 69.9° F. The slurry of ethane and frozen solid carbon dioxide is passed to optional solids settling separator 25 where a portion of the ethane may be separated from the carbon dioxide solids. As shown, the carbon dioxide solids and remaining ethane exit the settling separator through line 27 and the separated ethane exits through line 29 and is recovered.

The slurry in line 27 is passed to cryogenic wash tank 31 where the slurry is mixed with wash hydrocarbon introduced through inlet line 33. The wash hydrocarbon is a hydrocarbon with at least three carbon atoms. Propane and heavier hydrocarbons do not form an azeotrope with carbon dioxide. The wash liquid is introduced in a manner and in a quantity such that a substantial portion of the ethane in the solid carbon dioxide-ethane slurry is washed from the slurry with the wash hydrocarbon. The ethane that is washed from the slurry will be replaced with the heavier wash hydrocarbon. The slurry of carbon dioxide solids and wash hydrocarbon is passed from the wash unit through exit line 35. The mixture of ethane and wash hydrocarbon is removed through line 37. If additional wash hydrocarbon is needed, all or a portion of the ethane plus hydrocarbon mixture may be passed to a subsequent distillation column (not shown) to separate at least a portion of the heavier hydrocarbons for return directly or indirectly to wash tank 31.

As shown, the slurry of solid carbon dioxide and wash hydrocarbon is passed through heat exchanger 38 to second stage distillation column 39 where the liquid hydrocarbon is recovered through bottom liquid line 43 for return to the wash tank and the carbon dioxide is recovered after the column overhead effluent in line 41 is cooled in condenser 45. Part of the cooled effluent is recycled back to the column through recovery-reflux line 47. If the vapor pressures of carbon dioxide and the wash hydrocarbon are sufficiently different, the carbon dioxide may be separated in a simple gas separator.

In typical fashion distillation columns 13 and 39 are equipped with side heaters or reboilers represented by reboilers 49. These reboilers and overhead condensers 19 and 45 are used to balance the heat loads of the columns.

Reasonable variations and modifications are possible within the scope of this disclosure without departing from the spirit and scope of this invention.

The embodiments of the invention in which an exclusive property or privilege is claimed are defined as follows:

1. A method for separating a mixture of carbon dioxide and ethane derived from a prior separation stage, said method comprising:
   (a) cooling an azeotrope of carbon dioxide and ethane to form a first slurry of ethane and solid carbon dioxide, said azeotrope having been derived from a prior carbon dioxide separation stage;
   (b) mixing at least a portion of said first slurry with a first liquid hydrocarbon comprised of at least one hydrocarbon having at least three carbon atoms in a manner and quantity such that said liquid hydrocarbon washes a substantial portion of said ethane from said first slurry;
   (c) recovering a second slurry of solid carbon dioxide and hydrocarbon, said second slurry having less concentration of ethane than said first slurry, and
   (d) recovering a second liquid hydrocarbon, said second liquid hydrocarbon being comprised of said hydrocarbon liquid and ethane extracted from said first slurry.

2. In the method of claim 1 wherein the method includes the following additional step:
   (e) passing a fluid mixture comprised of carbon dioxide and ethane into a first distillation column to separate ethane from said mixture and to form an overhead azeotrope of carbon dioxide and ethane, said fluid mixture having been derived from a prior carbon dioxide separation stage, and said azeotrope forming at least a portion of the azeotrope used in step (a).

3. In the method of claim 2 wherein the method includes the following additional step:
   (f) separating at least a portion of the carbon dioxide in said second slurry from the hydrocarbons in said second slurry.

4. In the method of claim 3 where the method includes the following additional step:
   (g) separating at least a portion of the hydrocarbon from said second liquid hydrocarbon to form at least a portion of said first liquid hydrocarbon used in step (b).

5. In the method of claim 2 wherein the method includes the following additional step:
   (f) separating at least a portion of the carbon dioxide in said second slurry from the hydrocarbons in said second slurry.

6. In the method of claim 5 where the method includes the following additional step:
   (g) separating at least a portion of the hydrocarbon from said second liquid hydrocarbon to form at least a portion of said first liquid hydrocarbon used in step (b).

7. In the method of claim 2 where the method includes the following additional step:
   (f) separating at least a portion of the hdyrocarbon from said second liquid hydrocarbon to form at least a portion of said first liquid hydrocarbon used in step (b).

8. In the method of claim 1 wherein the method includes the following additional step:
   (e) separating at least a portion of the carbon dioxide in said second slurry from the hydrocarbons in said second slurry.

9. In the method of claim 8 where the method includes the following additional step:
   (f) separating at least a portion of the hydrocarbon from said second liquid hydrocarbon to form at least a portion of said first liquid hydrocarbon used in step (b).

10. In the method of claim 1 where the method includes the following additional step:
    (e) separating at least a portion of the hydrocarbon from said second liquid hydrocarbon to form at least a portion of said first liquid hydrocarbon used in step (b).

* * * * *